United States Patent [19]

Bricker

[11] Patent Number: 5,026,937
[45] Date of Patent: Jun. 25, 1991

[54] AROMATIZATION OF METHANE USING ZEOLITE INCORPORATED IN A PHOSPHORUS-CONTAINING ALUMINA

[75] Inventor: Jeffery C. Bricker, Buffalo Grove, Ill.

[73] Assignee: UOP, Des Plaines, Ill.

[21] Appl. No.: 459,162

[22] Filed: Dec. 29, 1989

[51] Int. Cl.$^5$ ............................. C67C 1/20; C67C 2/00
[52] U.S. Cl. ....................................... 585/415; 585/500
[58] Field of Search ................................ 585/415, 500

[56] References Cited

U.S. PATENT DOCUMENTS

| | | | |
|---|---|---|---|
| 4,523,049 | 6/1985 | Jones et al. | 585/500 |
| 4,590,321 | 5/1986 | Chu | 585/407 |
| 4,654,455 | 3/1987 | Chao | 585/415 |
| 4,665,251 | 5/1987 | Chu | 585/415 |
| 4,695,663 | 9/1987 | Hall et al. | 585/500 |
| 4,724,271 | 2/1988 | Martindale et al. | 585/415 |
| 4,761,511 | 8/1988 | Barlow | 585/415 |
| 4,766,264 | 8/1988 | Bennett et al. | 585/415 |
| 4,795,845 | 1/1989 | Martindale et al. | 585/415 |
| 4,814,533 | 3/1989 | Devries et al. | 585/415 |
| 4,891,463 | 1/1990 | Chu | 585/415 |

*Primary Examiner*—Helane E. Myers
*Attorney, Agent, or Firm*—Thomas K. McBride; John F. Spears, Jr.

[57] ABSTRACT

Methane is upgraded to aromatic hydrocarbons and other valuable $C_3$-plus hydrocarbons by contact with a catalyst comprising gallium and a ZSM-type zeolite incorporated in a phosphorous-containing alumina at relatively low temperature conditions.

10 Claims, No Drawings

AROMATIZATION OF METHANE USING ZEOLITE INCORPORATED IN A PHOSPHORUS-CONTAINING ALUMINA

FIELD OF THE INVENTION

The invention relates to a hydrocarbon conversion process used for upgrading methane into more valuable hydrocarbons. The invention specifically relates to a process for the conversion of methane into aromatic $C_6$ to $C_{10}$ hydrocarbons. The scope of the invention is preferably limited to aromatization of methane using a zeolitic catalyst incorporated in a phosphorus-alumina matrix in the substantial absence of free oxygen.

PRIOR ART

There has been a recognition in the prior art that it is desirable to convert methane into a higher molecular weight hydrocarbon. For instance, it is known that it is normally commercially unfeasible to transport methane produced with crude oil or natural gas from a well site to a distant location for consumption as fuel. Often the transportation problems relate to the extremely low temperatures needed to liquefy methane or to liquefy a gas mixture containing large amounts of methane. It is normally very costly to separate other light hydrocarbons such as ethane from methane and it is undesirable to admix methane with other hydrocarbons prior to transport. The result has been that large amounts of methane are essentially disposed of in a wasteful manner as by flaring without utilization of the hydrocarbonaceous nature of the methane.

U.S. Pat. No. 4,567,311 issued to L. DeVires et al. is believed pertinent for its teaching of the recognition of the general problem of methane utilization and also for its presentation of a process for the upgrading of methane using a specific silicon-containing catalyst. This reference provides an excellent discussion of the problems involved with methane utilization and provides a summary of the prior art relating to other methods of converting methane to ethylene or other $C_2+$ hydrocarbons.

U.S. Pat. No. 4,565,897 issued to B.R. Gane et al. is believed pertinent for its teaching of the conversion of $C_2$-plus hydrocarbons using a catalyst comprising a ZSM-5 variety zeolite and gallium. The catalyst employed within the process of the reference therefore shares two common characteristics with the preferred catalyst employed in the subject process.

U.S. Pat. No. 4,654,455 issued to T. Chao is believed pertinent for its teaching relative to the preparation and use of a catalyst similar to that employed in the subject process. The catalyst of this reference comprises a phosphorous-containing alumina, a gallium component and a crystalline aluminosilicate such as a ZSM zeolite. The reference is directed to the conversion of $C_2-C_5$ aliphatic hydrocarbons to aromatic hydrocarbons.

U.S. Pat. No. 4,727,206 issued to D.M. Clayson et al. is believed pertinent for its teaching in regard to the conversion of methane to aromatic hydrocarbons at 600-800 degrees C. using a catalyst which comprises an aluminosilicate such as a ZSM-5 variety zeolite which has been exchanged or loaded with (i) gallium or a compound thereof and (ii) a metal or a compound thereof from Group VIIB of the Periodic Table. The preferred group VIIB metal is rhenium. This reference is pertinent for its teaching at line 39-41 of column 1 that the feedstream may contain at least 50 percent and preferably at least 70 weight percent methane. The three examples all specify the aromatization of methane by contacting the catalyst with methane.

SUMMARY OF THE INVENTION

It has now been discovered that methane can be aromatized using a catalyst comprising a gallium-loaded zeolite bound in a phosphorus-modified alumina. The process operates at relatively low-severity conditions in the absence of oxygen. The catalyst is stable and suitable for multiple regenerations in a moving bed reactor/regenerator system.

One embodiment of the invention can be characterized as a process for the conversion of methane into $C_3$-plus hydrocarbons which comprises contacting a feed stream, which is rich in methane, with a catalyst comprising a crystalline aluminosilicate incorporated within a phosphorous-containing alumina at conversion conditions which include a temperature of 550-750° C., a pressure less than 10 atmospheres absolute and a gas hourly space velocity of about 400-7,500 $hr^{-1}$, and recovering product $C_2$-plus hydrocarbons.

DETAILED DESCRIPTION OF THE INVENTION

As mentioned briefly above, methane is often considered to be of relatively low value. Among the reasons for this is a low heat of combustion per volume, the difficulty associated with liquefying methane or methane-containing hydrocarbon mixtures, the relative inertness which has limited its use as chemical feedstock and the problems encountered in transporting large volumes of methane. It has been estimated that the methane produced with crude oil and subsequently flared (burned) for disposal is equivalent to 1 million barrels of oil per day. At the same time, it is realized that additional large amounts of methane are available from natural gas, coal beds and as by-products of petroleum refining. Methane can also be synthesized. It is an objective of the subject invention to provide a process for upgrading methane into higher molecular weight hydrocarbons having greater economic value and which are more easily transported or stored and which are suitable as feed stocks in present commercial petrochemical manufacturing processes. It is also an objective of the subject invention to provide a process for converting methane into aromatic hydrocarbons.

The subject invention comprises contacting the methane-containing feed stream with a solid catalyst maintained at conversion conditions in a reaction zone. The feed stream can be a stream of essentially pure methane although even a pure methane stream is likely to contain some small amount, up to about 1.5 mole percent or more, of higher hydrocarbons due to the less than perfect separations which must be accepted in commercial scale processes. The feed stream could also contain nitrogen and possibly other inorganic species, but is preferably free of any compound containing sulfur. The feed stream may contain recycled methane and also recycled low carbon number hydrocarbons such as ethane, ethylene, propane and butane. It is preferred that the feed stream is rich in methane. As used herein the term "rich" is intended to indicate a molar concentration of the indicated compound or class of compounds above 50 percent. It is more preferred that the feed stream contain over 80 mole percent methane and it is highly preferred that the feed stream contain over 95 mole percent methane. The remaining portion (non-methane portion) is preferably made up from paraffinic and/or olefinic hydrocarbons.

In a limited embodiment of the invention, the feed stream may contain hydrogen. In this embodiment of the invention, it is preferred that the feed methane be adjusted to contain at least 0.5 mole percent hydrogen. A highly preferred hydrogen concentration in the feed to the reaction zone, if there is a hydrogen cofeed, is from about 2 to 10 mole percent.

The feed stream is brought into contact with the catalyst in a reaction zone which may comprise a single reactor or several separate reactors. The catalyst may be in a fluidized state within the reactor or maintained as an immobile or fixed bed. It is preferred that the catalyst is retained in a radial flow moving bed reactor similar in general nature to those described in U.S. Pat. Nos. 3,907,511; 4,040,794; 4,411,870 and 4,567,023, Which are incorporated herein by reference. A moving bed reactor system has the advantage of allowing continuous removal of catalyst from the reactor, with the withdrawn catalyst being replaced by fresh or regenerated catalyst. This allows the process to be operated at uniform conditions and produce an effluent stream of uniform composition at all times while onstream. The use of a moving bed reactor eliminates shutdowns for catalyst replacement or regeneration and therefore provides better equipment utilization at a lower labor cost. Finally, the use of a moving bed allows operation at more severe conditions or any set of conditions which causes such significant catalyst deactivation that the process would be commercially impractical in a fixed-bed system. The beds of methane conversion catalyst are preferably stacked directly above each other to allow transport of catalyst downward by gravity.

Moving bed reactor systems are normally coupled with a moving bed or continuous catalyst regeneration system. An example of such a system is provided in U.S. Pat. No. 3,978,150. Further information on the transfer of catalyst may be obtained from available reference sources such as U.S. Pat. Nos. 4,110,197 and 4,403,909. The regeneration of catalysts in a moving bed system is described in detail in U.S. Pat. Nos. 4,094,814 and 4,094,815. Although these references are directed primarily to catalytic reforming, their teaching in regard to reactor design and catalyst handling is applicable to all similar moving catalyst bed processes. U.S. Pat. No. 4,724,271 is also a beneficial source of instruction on catalyst regeneration as it is directed to regeneration of a catalyst similar to the methane conversion catalyst described below.

The upgrading of methane to higher hydrocarbons involves endothermic reaction steps. As a result the overall reaction to produce aromatics is very endothermic. The cooling effect caused by the reaction will lower the reactant temperature enough to greatly reduce the reaction rate if heat is not provided in some manner. The heat required to sustain the reaction could be supplied by indirect heat exchange against a heating fluid flowing through the reaction zone or surrounding the catalyst. For instance, the catalyst could be inserted in relatively small e.g. 2.5 to 5 cm diameter tubes surrounded by a circulating heat transfer fluid in order to maintain the catalyst bed at a relatively uniform temperature. This form of heating, however, is not preferred as it is not believed compatible with the preferred moving bed reactor design.

The preferred method of supplying heat to the reaction is the provision of several sequential reaction zones, preferably three to five, with means to reheat the reactants provided between the reaction zones. In this interstage reheating the reactant effluent of a first bed of catalyst is heated to the desired inlet temperature of a second downstream bed of catalyst.

One method of interstage reheating comprises the use of indirect heat exchange. In this method the effluent from an upstream reaction zone is passed through a heat exchanger in which it is heated, and the reactants are then passed into the subsequent reactor. This method is widely employed on moving bed reforming processes as referred to above. The high temperature fluid employed in this indirect heat exchange method may be high temperature steam, combustion gases, a high temperature process stream or other readily available high temperature fluids. This method of interstage heating does not dilute the reactants but does impose some pressure drop in the system and can expose the reactants to undesirably high temperatures.

Another method of interstage heating is the oxidative reheat method. This involves the admixture of a controlled amount of oxygen into the reactants and the selective oxidation of hydrogen. The driving force for employing the oxidative reheat method is the recognition that the combustion of the hydrogen generated in an aromatization process normally performs two functions which are beneficial in an endothermic hydrogen-producing process. First, the consumption of the hydrogen is beneficial in shifting the equilibrium of the reaction to favor increased amounts of conversion. Second, the combustion of the hydrogen will release heat sufficient to reheat the reactants to the desired methane conversion conditions. The oxidation is preferably accomplished in the presence of a catalyst which selectively promotes the oxidation of hydrogen as compared to the destructive combustion or oxidation of the more valuable feed and product hydrocarbons.

Oxidative reheating is the preferred method of reheating the reactants if more than one stage of conversion is performed in the process. The amount of oxygen combustion required is readily calculated on the basis of the mass flow rate of the reactants and the required temperature increase. Essentially 100 percent conversion of the added oxygen prior to the contact of the reactants with the methane aromatization catalyst is preferred. The oxidation step is preferably performed using a radial flow bed of catalyst located a small distance upstream of the aromatization catalyst bed. The bed of selective oxidation catalyst is most preferably located adjacent to the aromatization catalyst sharing a common vertical catalyst retention screen. The oxidation catalyst bed is preferably fixed in place but could be a moving bed system. The required oxygen can be added from a variety of gases including pure oxygen and air. Pure oxygen has the advantage of not adding nitrogen and other hard-to-condense gases to the reactants and hence makes product separation and recovery easier. The added oxygen is preferably diluted with steam to minimize the possibility of an explosion or localized high temperatures due to oxygen concentration profiles. The oxidation catalyst bed is preferably located in the centerpipe of the annular conversion catalyst bed.

The oxidation catalyst employed in the subject process to promote the interstage hydrogen oxidation may be any commercially suitable catalyst which meets the required standards for stability and activity and which possesses high selectivity for the oxidation of hydrogen as compared with the oxidation of the feed or product hydrocarbon. That is, the oxidation catalyst must have a high selectivity for the oxidation of hydrogen with only small amounts of the feed or product hydrocarbon being oxidized.

The oxidation catalyst will preferably have a different composition than the aromatization catalyst. The preferred oxidation catalyst comprises a Group VIII noble metal and a metal or metal cation which possesses a crystal ionic radius greater than 1.35 angstroms, with both of these materials being present in small amounts on a refractory solid support. The preferred Group VIII metals are platinum and palladium, but the use of ruthenium, rhodium, osmium and iridium is also contemplated. The Group VIII metal is preferably present in an amount equal to 0.01 to 5.0 wt.% of the finished catalyst. The metal or metal cation having a radius greater than 1.35 angstroms is preferably chosen from Groups IA or IIA and is present in an amount equal to about 0.01 to about 20 wt.% of the finished catalyst. This component of the catalyst is preferably lithium, but the use of other metals including barium, rubidium, or cesium is also contemplated. The oxidation catalyst may also contain a Group IVA component, preferably tin, at 0.01 to 10 wt.%.

The preferred solid support for the oxidation catalyst is alumina having a surface area between 1 and 300 m$^2$/g, an apparent bulk density of between about 0.2 and 1.5 g/cc, and an average pore size greater than 20 angstroms. The metal-containing components are preferably impregnated into solid particles of the solid support by immersion in an aqueous solution followed by drying and calcination at a temperature of from about 500° to 600° C. in air. The support may be in the form of spheres, pellets or extrudates. The total amount of oxidation catalyst present within a reaction zone is preferably less than 30 wt.% of the total amount of methane conversion catalyst and more preferably is between 5 and 15 wt.% of this total amount of methane conversion catalyst. Further information on the composition of a suitable selective oxidation catalyst is provided in U.S. Pat. Nos. 4,435,607 and 4,565,898, which are incorporated herein by reference. It is preferred that the oxidation catalyst is retained in a fixed bed adjacent to the methane conversion catalyst.

The conditions utilized during the contacting of the reactant streams with the different beds of oxidation catalyst will be set to a large extent by the desired methane conversion conditions. The preferred outlet temperature of any bed of oxidation catalyst is the preferred inlet of the immediately downstream bed of aromatization catalyst. The temperature rise across any bed of oxidation catalyst is preferably at least 100 Celsius degrees to compensate for the cooling described below. Without such cooling only a smaller amount of heating is required in the oxidation catalyst bed. The liquid hourly space velocity, based on the liquid hydrocarbon charge at 60° F., is preferably between 2 and 10 hr$^{-1}$.

The subject process is preferably operated at relatively low temperatures for methane conversion. A portion of this preference results from the desire to avoid the metallurgical and processing problems associated with high temperatures. A more fundamental reason for this preference is the increased selectivity for hydrogen oxidation at lower temperatures. At 500 degrees C. the selectivity is about 100 percent but this drops rapidly above 600 degrees C. and can be as low as 20 percent at 850 degrees C. It is therefore preferred to operate at a temperature below 675 degrees C. This is intended to refer to the temperature at the outlet of an oxidation catalyst bed, which is expected to be the highest temperature in the oxidation catalyst bed.

One objective of using selective hydrogen combustion within the overall process is to shift the equilibrium to favor more methane conversion by consuming one of the reaction products. It is to be noted that the greatest benefit of hydrogen consumption is achieved when the reaction products are close to equilibrium. The production of one mole of benzene yields nine moles of hydrogen. The removal of hydrogen can therefore have a large impact on conversion and is very beneficial. It is accordingly preferred to cool the reactants prior to or during the selective hydrogen combustion step as by indirect heat exchange as taught in U.S. Pat. No. 4,739,124, which is incorporated herein for this teaching. Use of this technique should greatly increase the rate of methane conversion which can be achieved. Calculated values for a four methane reaction zone process are in the range of 15-22 wt percent conversion when interstage cooling and selective oxidation are employed.

One feature which distinguishes the subject process from the above cited reference is that it is necessary to cool to a very extreme degree which is beyond that required for ethane, propane or butane dehydrogenation in order to achieve these high methane conversion rates. Cooling may be used to reduce the reactant temperature down to about 250 degrees C. and possibly even 200 degrees C. It is preferred to cool the reactants, or to remove heat equivalent to cooling, by at least 100 C. degrees. Cooling by up to about 400 C. degrees may be used, with a preferred range of cooling being from about 250 to 350 C. degrees.

The methane conversion catalyst is preferably spherical. Refractory inorganic oxide particles of spherical shape offer numerous advantages when employed as a support or carrier material for catalytically active metallic components. When disposed in a fixed bed in a reaction or contact zone, the spherical particles permit more uniform packing and reduce the tendency of the reactant stream to channel through the catalyst bed. When employed in a moving bed type of operation, that is, where the particles are transported from one zone to another by the reactants, an extraneous carrying medium or gravity, the spheroidal particles have a further advantage in that there are no sharp edges to break or wear off during processing, thus creating a tendency to restrict the flow through process equipment.

One preferred method of preparing the refractory inorganic oxide as spheroidal particles is by the gelation of a hydrosol precursor of the refractory inorganic oxide in accordance with the oil-drop method. Suitable hydrosols may be prepared by the general method whereby an acid salt of an appropriate metal is hydrolyzed in aqueous solution and the solution treated at conditions to reduce the acid compound concentration thereof, as by neutralization. The resulting olation reaction yields inorganic polymers of colloidal dimension dispersed and suspended in the remaining liquid. For example, an amorphous alumina hydrosol can be prepared by the hydrolysis of an acid salt of aluminum, such as aluminum chloride, in aqueous solution, and treating said solution at conditions to reduce the resulting chloride compound concentration thereof, as by neutralization, to achieve an aluminum/chloride compound weight ratio from about 0.70:1 to about 1.5:1.

The aluminum chloride hydrosol is typically prepared by digesting aluminum in aqueous hydrochloric acid and/or aluminum chloride solution at about reflux temperature, usually from about 80° to about 105° C., and reducing the chloride compound concentration of the resulting aluminum chloride solution by the device of maintaining an excess of the aluminum reactant in the reaction mixture as a neutralizing agent. The alumina hydrosol is an aluminum chloride hydrosol variously referred to as an aluminum oxychloride hydrosol, aluminum hydroxychloride hydrosol, and the like, such as is formed when utilizing aluminum metal as a neutralizing agent in conjunction with an aqueous aluminum chloride solution. In any case, the aluminum chloride hydrosol is prepared to contain aluminum in from about a 0.70:1 to about 1.5:1 weight ratio with the chloride compound content thereof.

In accordance with the method of the present invention, a phosphorus-containing compound is added to the above-described hydrosol to form a phosphorus-modified hydrosol. Representative phosphorus-containing compounds which may be utilized in the present invention include $H_3PO_4$, $H_3PO_2$, $H_3PO_3$, $(NH_4)H_2PO_4$, $(NH_4)_2HPO_4$, $K_3PO_4$, $K_2HPO_4$, $KH_2PO_4$, $Na_3PO_4$, $Na_2HPO_4$, $NaH_2PO_4$, $PX_3$, $RPX_2$, $R_2PX$, $R_3P$, $X_3PO$, $(XO)_3PO$, $(XO)_3P$, $R_3PO$, $R_3PS$, $RPO_2$, $RPS_2$, $RP(O)(OX)_2$, $RP(S)(SX)_2$, $R_2P(O)OX$, $R_2P(S)SX$, $RP(OX)_2$, $RP(SX)_2$, $ROP(OX)_2$, $RSP(SX)_2$, $(RS)_2PSP(SR)_2$, and $(RO)_2POP(OR)_2$, where R is an alkyl or aryl, such as a phenyl radical, and X is hydrogen, R, or halide. These compounds include primary, $RPH_2$, secondary, $R_2PH$ and tertiary, $R_3P$ phosphines such as butyl phosphine, the tertiary phosphine oxides $R_3PO$, such as tributylphosphine oxide, the tertiary phosphine sulfides, $R_3PS$, the primary, $RP(O)(OX)_2$, and secondary, $R_2P(O)OX$, phosphonic acids such as benzene phosphonic acid, the corresponding sulfur derivatives such as $RP(S)(SX)_2$ and $R_2P(S)SX$, the esters of the phosphonic acids such as dialkyl phosphonate, $(RO)_2P(O)H$, dialkyl alkyl phosphonates, $(RO)_2P(O)R$, and alkyl dialkyl-phosphinates, $(RO)P(O)R_2$; phosphinous acids, $R_2POX$, such as diethylphosphinous acid, primary, $(RO)P(OX)_2$, secondary, $(RO)_2POX$, and tertiary, $(RO)_3P$, phosphites, and esters thereof, such as the monopropyl ester, alkyl dialkylphosphinites, $(RO)PR_2$ and dialkyl alkylphosphinite, $(RO)_2PR$, esters. Corresponding sulfur derivates may also be employed including $(RS)_2P(S)H$, $(RS)_2P(S)R$, $(RS)P(S)R_2$, $R_2PSX$, $(RS)P(SX)_2$, $(RS)_2PSX$, $(RS)_3P$, $(RS)PR_2$ and $(RS)_2PR$. Examples of phosphite esters include trimethylphosphite, triethylphosphite, diisopropylphosphite, butylphosphite, and pyrophosphites such as tetraethylpyrophosphite. The alkyl groups in the mentioned compounds preferably contain one to four carbon atoms.

Other suitable phosphorus-containing compounds include ammonium hydrogen phosphate, the phosphorus halides such as phosphorus trichloride, bromide, and iodide, alkyl phosphorodichloridites, $(RO)PCl_2$, dialkylphosphorochloridites, $(RO)_2PCl$, dialkylphosphinochloridites, $R_2PCl$, alkyl alkylphosphonochloridates, $(RO)(R)P(O)Cl$, dialkylphosphinochloridates, $R_2P(O)Cl$ and $RP(O)Cl_2$. Applicable corresponding sulfur derivatives include $(RS)PCl_2$, $(RS)_2PCl$, $(RS)(R)P(S)Cl$ and $R_2P(S)Cl$.

A 1:1 molar ratio of aluminum to phosphorus in the phosphorus-modified sol corresponds to a final calcined spheroidal particle composition containing 24.74 wt. % phosphorus and 20.5 wt. % aluminum, while a 1:100 molar ratio corresponds to a final composition of 0.6 wt. % phosphorus and 52.0 wt. % aluminum.

In accordance with the above description, phosphorus-modified alumina particles can be prepared by a method which comprises admixing the alumina hydrosol with a phosphorus-containing compound, the phosphorus to aluminum molar ratio in the resulting phosphorus-modified admixture being from 1:1 to 1:100 on an elemental basis and subsequently gelling said admixture to obtain said particles.

Gelation can be effected by commingling the phosphorus-modified admixture with a gelling agent which is hydrolyzable at an elevated temperature, dispersing said commingled admixture as droplets in a suspending medium under conditions effective to transform said droplets in a suspending medium into hydrogel particles, aging said hydrogel particles in a suspending medium, washing said hydrogel particles with water, drying, and calcining said hydrogel particles to obtain phosphorus-modified alumina spheroidal particles. Alternatively gelation may be carried out by spray drying the above-described phosphorus-modified alumina hydrosol or commingling the subject hydrosol with a gelling agent and then spray drying. Spray drying is typically carried out at a temperature of 800° F. (425° C.) to 1400° F. (760° C.) at about atmospheric pressure.

The gelling agent is typically a weak base which, when mixed with the hydrosol, will cause the mixture to set to a gel within a reasonable time. In this type of operation, the hydrosol is typically set by utilizing ammonia as a neutralizing or setting agent. Usually, the ammonia is furnished by an ammonia precursor which is added to the hydrosol. The precursor is suitably hexamethylenetetramine, or urea, or mixtures thereof, although other weakly basic materials which are substantially stable at normal temperatures, but decompose to form ammonia with increasing temperature, may be suitably employed. It has been found that mixing equal volumes of the hydrosol and of the hexamethylenetetramine solution is satisfactory, but it is understood that this may vary somewhat. The use of a smaller amount of hexamethylenetetramine solution tends to result in soft spheres while, on the other hand, the use of larger volumes of base solution results in spheres which tend to crack easily. Only a fraction of the ammonia precursor is hydrolyzed or decomposed in the relatively short period during which initial gelation occurs.

An aging process is preferably subsequently employed. During the aging process, the residual ammonia precursor retained in the spheroidal particles continues to hydrolyze and effect further polymerization of the hydrogel whereby desirable pore characteristics are established. Aging of the hydrogel is suitably accomplished over a period of from about 1 to about 24 hours, preferably in the oil suspending medium, at a temperature of from about 60° to about 150° C. or more, and at a pressure to maintain the water content of the hydrogel spheres in a substantially liquid phase. The aging of the hydrogel can also be carried out in aqueous $NH_3$ solution at about 95° C. for a period up to about 6 hours. Following the aging step, the hydrogel spheres may be washed with water containing ammonia.

After the hydrogel particles are aged, a drying step is effected. Drying of the particles is suitably effected at a temperature of from 38° to about 205° C. Subsequent to the drying step, a calcination step is effected at a temperature of from about 425° to about 760° C. for 2 to 12 hours or more which may be carried out in the presence of steam. The calcined particles may then be impregnated with other catalytic components. Further information on the preparation of the phosphorouscontaining alumina component may be obtained from U.S. Pat. Nos. 4,636,483 and 4,654,455 which are incorporated herein by reference.

The phosphorus-modified alumina should possess a high surface area and a high micropore volume. The total pore volume of porous refractory inorganic oxide particles utilized in a catalyst support is typically expressed in terms of pore size distribution, that is, in terms of the pore volume attributable to macropores and pore volume attributable to micropores. The total pore volume is determined by the mercury intrusion method. The total surface area of the refractory inorganic oxide particles is a function of the micropore volume, substantially all of the surface area being associated with pores of less than about 600 Angstroms in diameter. The surface areas of the phosphorous-modified alumina used in the present invention is believed substantially greater than the surface area of conventional gamma-alumina manufactured by the oil-drop method and alumina-aluminum phosphates by precipitation methods. The conventional oil-dropped alumina possesses a surface area of up to about 250 m²/g. The finished particles manufactured for use with the present invention possess a surface area of up to about 450 m²/g. A minimum surface area of 300 m²/g is preferred.

The catalytic composite employed in the subject invention may accordingly be characterized as a catalytic composite having low cracking activity and comprising a pentasil zeolite and an amorphous phosphorus-modified alumina having a molar ratio on an elemental basis of phosphorus to aluminum of from about 1:1 to 1:100 and a surface area of from about 140 to 450 m²/g; said hydrogel being formed by the gelation of a homogeneous hydrosol having an aluminum to chloride compound weight ratio of from about 0.70:1 to 1.5:1. The catalyst preferably has a surface area of from about 225 to 450 m²/g and a molar ratio of phosphorus to aluminum on an elemental basis of about 1:1.6 to 1:100. The catalyst preferably contains at least 10 wt percent phosphorous-modified alumina and more preferably at least 15 wt percent phosphorous-modified alumina.

The zeolitic component of the catalyst may be incorporated into the hydrosol prior to dropping. The zeolites are, of course, crystalline, three-dimensional, stable structures containing a large number of uniform openings or cavities interconnected by smaller, relatively uniform holes or channels. The effective pore size of synthetic zeolites is between 6 Angstroms and 15 Angstroms in diameter. The overall formula for the zeolites can be represented as follows:

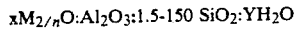

$xM_{2/n}O:Al_2O_3:1.5\text{-}150\ SiO_2:YH_2O$ where M is a metal cation and n is its valence and x varies from 0 to 1 and y is a function of the degree of dehydration and varies from 0 to 9, M is preferably a rare earth metal cation such as lanthanum, cerium, praseodymium, neodymium, etc., or mixtures of these.

The zeolite component of the catalyst used in the present invention may be a pentasil crystalline aluminosilicate zeolite. "Pentasil" is a term used to describe a class of shape selective zeolites. This novel class of zeolites is well known to the art and is typically characterized by a silica-to-alumina ratio of at least about 12. Suitable descriptions of the pentasils may be found in U.S. Pat. Nos. 4,159,282; 4,163,018; and 4,278,565, all of which are incorporated herein by reference. Of the pentasil zeolites, the preferred ones are ZSM-5, ZSM-8, ZSM-11, ZSM-23, and ZSM-35, with ZSM-5 being particularly preferred. Zeolite ZSM-5 is described in greater detail in U.S. Pat. Nos. 3,702,886 and Re. 29,948. ZSM-11 is described in U.S. Pat. No. 3,709,979 and ZSM-5/ZSM-11 intermediate compositions are described in U.S. Pat. No. 4,229,424 which is incorporated herein by reference. A listing of patents relevant to other ZSM zeolites is found in U.S. Pat. No. 4,657,874. Omega zeolites may be employed in the subject catalyst. Zeolite Omega is described in U.S. Pat. No. 4,780,436.

The term "zeolite" as used herein contemplates not only aluminosilicates, but substances in which the aluminum is replaced in part or in whole by gallium and substances in which the silicon is replaced by germanium. The preferred zeolites will have a silicon to aluminum framework ratio above 20:1.

The methane conversion catalyst will preferably contain a significant amount of the zeolite component. The catalyst should contain at least 40 wt. percent zeolite. A ZSM-5 content over 50 wt percent is highly preferred, with concentrations of about 65 to about 85 wt percent being contemplated. A total zeolite content less than 90 wt percent is preferred, with the remainder of the methane conversion catalyst being the metal component(s) and phosphorous-containing alumina.

The methane conversion catalyst used in the subject process preferably contains a metal component which may be added by impregnation or ion exchange after the zeolite-alumina composite is formed. The preferred metal component is gallium or a gallium compound such as an oxide or halide. Other metal components contemplated for use in the catalyst comprise platinum, rhodium, ruthenium and iridium or a mixture of two or more of these metals. The catalyst may therefore comprise a mixture of gallium and platinum, gallium and iridium, platinum and iridium, platinum and rhodium, etc. The final finished catalyst composite should contain less than 9 wt. percent metal component as measured on an elemental basis. It is preferred that the finished composite contains from 0.1 to about 5.0 wt.% total metal component. A preferred concentration for gallium on a finished methane conversion catalyst is from about 0.1 to about 2.0 wt. percent.

It is presently preferred that the methane conversion catalyst does not contain a catalytically effective amount of a metal other than those set out above. Accordingly, the concentration of Group VIB and Group VIIB metals, iron, cobalt and nickel are preferably less than 0.1 wt. percent. References herein to the Periodic Table are to that form of the table presented inside the front cover of the 4th edition of *Chemical Engineers' Handbook*, McGraw-Hill, 1963.

The metal component can be added to the catalyst by methods well known in the art. Preferably the metal component is added by a method which tends to locate the metal component on or near the zeolitic component. One suitable method is to immerse the particles in an aqueous solution of a water soluble metal salt such as a chloride of the metal. The particles are then drained and calcined.

It is preferred that the metal component(s) are uniformly distributed throughout the finished catalyst rather than surface impregnated.

The effluent of the final contacting step may be separated to recover the products using several techniques known to those skilled in the art of hydrocarbon conversion process design. A presently preferred method of product recovery comprises the steps of cooling the effluent by indirect heat exchange for heat recovery and then by exchange against a cooling media such as air to a temperature below 150° F. to effect condensation of many of the $C_4$-plus and most of the $C_6$-plus product hydrocarbons. The liquid hydrocarbons are then sent to fractional distillation columns which will normally comprise a stripping column and one or more product separation columns. The uncondensed portion of the effluent stream is compressed and further cooled to recover additional product hydrocarbons. Cryogenic (cold box) technology can be employed to separate the hydrogen and light hydrocarbons (methane, ethane, ethylene, etc.) which remain in the uncondensed gases. This overall flow would resemble portions of that shown in U.S. Pat. No. 4,634,799. An alternative method of processing the gases remaining after condensation of hydrocarbons present in the reaction zone effluent stream is shown in U.S. Pat. No. 4,528,412. This is an "autorefrigeration" method wherein the gas is compressed, dried, cooled and separated into condensate liquid and vapor phases. The resultant cool vapor is then expanded to effect further cooling and condensation of additional hydrocarbon liquids.

More than one product stream may be recovered from the process. For instance, the $C_4$-plus hydrocarbons produced in the process may be separated into $C_6$-minus and $C_6$-plus fractions to concentrate the aromatic product hydrocarbons into a single process stream. Light and heavy aromatic fractions may also be withdrawn separately. Hydrogen is also a valuable product of the process. It may be recovered in the above described manner or by the use of adsorptive separation, such as a pressure-swing adsorption unit, or by the use of membrane separation technology.

One or more of the components of the reaction zone may be recycled to the inlet of the reaction zone from the product recovery facilities. These products may be recycled individually or in admixture. One embodiment of the subject process comprises the recycling of low molecular weight hydrocarbons. For instance, ethane and propane or ethane and ethylene recovered from the final reaction zone effluent stream may be recycled by admixture into the methane feed stream. As a limited embodiment of the present invention, the hydrocarbon recycle stream is contacted with portions of the catalyst which are maintained at preferred conditions for further hydrocarbon upgrading rather than initial methane conversion. That is, only a portion of the catalyst descending through the preferred radial flow multibed moving bed reactor would be contacted with recycle hydrocarbons. For instance, the recycled hydrocarbons may be passed into the third or fourth reaction zone in a series of reaction zones rather than into the first reaction zone. This contacting may be done at conditions which differ in temperature and space velocity from the conditions employed in the reaction zones being used primarily for the conversion of methane. In general the conversion of propane and butane to aromatics is performed at a temperature of 400 to 550 degrees C. and a liquid hourly space velocity of about 0.5 to about 2.0 $hr^{-1}$.

As mentioned above, in another embodiment of the invention hydrogen is charged to the initial reaction zone in admixture with the feed methane. In this embodiment the combined feed stream should contain at least 0.5 mole % hydrogen. Fresh or recycled hydrogen is charged to the initial reaction zone at a rate sufficient to provide a hydrogen to hydrocarbon mole ratio greater than 0.005:1.0 and preferably above 0.02:1.0. The production of hydrogen within the process will normally result in the reaction zone effluent stream containing a higher ratio of hydrogen to hydrocarbon than the combined feed stream. The consumption of methane will also increase the ratio of hydrogen to hydrocarbons.

One embodiment of the invention may accordingly be characterized as a process for aromatization of methane which comprises the steps of passing a combined feed stream, which comprises over 50 mole percent methane and added hydrogen, into a reaction zone having at least one bed of solid catalyst comprising a pentasil zeolite and phosphorous-containing alumina at inlet conversion conditions which include a temperature of about 600–675° C., a pressure less than 10 atmospheres absolute, a hydrogen to hydrocarbon mole ratio of between 0.005 and 0.1 to 1 and a gas hourly space velocity of 400–7,500 $1$ $hr^{-1}$ and producing a reaction zone effluent stream comprising methane, hydrogen, at least 3 mole % $C_2$ hydrocarbons and at least 5 mole % $C_6$–$C_8$ aromatic hydrocarbons, recovering $C_6$–$C_8$ aromatic hydrocarbons as a product, and recycling a portion of the hydrogen present in the effluent stream to the reaction zone.

The methane conversion reaction is promoted by low pressures. An operating pressure less than 2 atmospheres absolute is preferred. More preferred is an outlet pressure of the last methane conversion zone of from 0.4 to 1.5 atmospheres absolute.

The use of oxidative reheat will result in the reaction zone effluent stream containing water vapor. It is presently preferred that no steam is intentionally added to the reaction zone as by admixture into the feed stream and that all recycle streams are relatively dry. This preference recognizes that an equilibrium amount of water vapor may be present in some recycled vapor streams if no specific drying step is provided. The only exception to this preference is any steam used to dilute oxygen charge to the selective combustion catalyst.

The use of oxidative reheat could cause some small amount of oxygen to unintentionally reach the methane conversion catalyst. However, the methane conversion reaction is preferably performed in the substantial absence of oxygen. That is, the reactants entering the methane conversion catalyst bed should contain less than 0.1 mole percent oxygen.

The performance of the subject process is further illustrated by this example of small scale pilot plant results. In this test 5.31 grams of the preferred catalyst comprising 80 wt.% ZSM-5 zeolite and 1.0 wt.% gallium was used. The remainder of the catalytic composite was the phosphorous-containing alumina described herein. The composite was formed by the oil dropping method set out above with the zeolite powder admixed into the alumina sol prior to formation of the spheres. The test was performed using spheres of about 0.16 cm diameter. The catalyst was contacted with a stream of essentially 100 mole percent methane at a flow rate of about 1.4 $hr^{-1}$ LHSV at an inlet temperature of approximately 750 degrees C. The reactor was operated at atmospheric pressure (0 psig) at the outlet. A single bed of catalyst surrounded by an electrical heating furnace was employed.

The effluent of the reaction zone was cooled to −78° C. to condense product hydrocarbons. The gas and liquid phases were analyzed to obtain product distribution data provided below in Table The overall methane conversion was 3.5 mole percent in the single pass and the selectivity to $C_2$-plus hydrocarbons was 72 percent. It was noted that the reaction products ranged from ethylene to $C_{10}$-plus hydrocarbons including naphthalene but are relatively low in aliphatic hydrocarbons. The process should provide a high percentage of aromatic hydrocarbons, with yields over 50 weight percent aromatics being preferred. The selectivity to coke was 28 wt. percent.

TABLE 1

| Product Distribution | Wt. Percent |
| --- | --- |
| ethylene | 11.1 |
| ethane | 2.8 |
| $C_3$ | not detected |
| $C_4$ | not detected |
| $C_5$ | not detected |
| $C_6$ | not detected |
| benzene | 33.4 |
| toluene | not detected |
| xylenes | not detected |
| naphthalene | 52.7 |

At the high temperature employed in this test the presence of propane, butane or xylene in the product distribution is expected to be very small. Propane and butane are unstable and xylene will be thermally dealkylated. This is borne out by the analysis of the effluent as shown above. The level of detection of the on-line analytical instruments was 0.1 wt. percent. The operating temperature of the reaction zone will have a significant impact on the product distribution.

What is claimed:

1. A process for aromatization of methane which comprises the steps of passing a feed stream, which comprises over 0.5 mole percent hydrogen and 50 mole percent methane, into a reaction zone having at least one bed of solid catalyst comprising a pentasil zeolite and phosphorous-containing alumina at conversion conditions which include a temperature of about 550-750° C., a pressure less than 10 atmospheres absolute and a gas hourly space velocity of 400-7,500 hu$^{-1}$ and producing a reaction zone effluent stream comprising methane, hydrogen, at least 3 mole % $C_2$ hydrocarbons and at least 5 mole % $C_6$-$C_8$ aromatic hydrocarbons, and recovering $C_6$-$C_8$ aromatic hydrocarbons as a product.

2. A process in accordance with claim 1 wherein the catalyst comprises a ZSM zeolite.

3. A process in accordance with claim 1 wherein the catalyst comprises about 0.1 to about 2.0 wt.% gallium.

4. A process in accordance with claim 1 the catalyst contains a zeolite having a silicon to aluminum ratio above 20:1.

5. A process in accordance with claim 1 wherein the catalyst comprises 1.0 to 20 wt.% phosphorous.

6. A process in accordance with claim 5 wherein the catalyst contains at least 40 wt. percent zeolite.

7. A process for aromatization of methane which comprises the steps of passing a feed stream, which comprises over 50 mole percent methane, and at least 0.5 mole percent added hydrogen into a reaction zone having at least one bed of solid methane conversion catalyst comprising a zeolite and phosphorous-containing alumina at inlet conversion conditions which include a temperature of about 600-675° C., a pressure less than 10 atmospheres absolute and a gas hourly space velocity of 400-7,500 hr$^{-1}$ and producing a reaction zone effluent stream comprising methane, hydrogen, at least 3 mole % $C_2$ hydrocarbons and at least 5 mole % $C_6$-$C_8$ aromatic hydrocarbons, recovering $C_6$-$C_8$ aromatic hydrocarbons as a product, and recycling a portion of the hydrogen present in the effluent stream to the reaction zone.

8. A process in accordance with claim 7 wherein the catalyst comprises a ZSM zeolite.

9. A process in accordance with claim 8 wherein the catalyst comprises over 50 wt percent ZSM-5 zeolite.

10. A process in accordance with claim 7 wherein the catalyst comprises about 0.1 to about 2.0 wt.% gallium.

* * * * *